United States Patent
Wojtowicz et al.

(10) Patent No.: US 6,321,586 B1
(45) Date of Patent: Nov. 27, 2001

(54) CONVEYOR FRICTION MEASUREMENT AND CLEANING SYSTEM

(75) Inventors: Edward A. Wojtowicz, Bryn Mawr; Clifford J. Bader, West Chester, both of PA (US)

(73) Assignee: Lockheed Martin Federal Systems, Inc., Manassas, VA (US)

( * ) Notice: Subject to any disclaimer, the term of this patent is extended or adjusted under 35 U.S.C. 154(b) by 0 days.

(21) Appl. No.: 09/243,529

(22) Filed: Feb. 1, 1999

(51) Int. Cl.$^7$ .............................. G01N 19/02; G01N 3/56
(52) U.S. Cl. ............................................................. 73/9
(58) Field of Search ................... 73/9, 7, 37.7; 198/839, 198/499, 496

(56) References Cited

U.S. PATENT DOCUMENTS

| | | | |
|---|---|---|---|
| 2,990,713 | 7/1961 | Heffelfinger et al. | 73/9 |
| 3,152,468 | 10/1964 | Powell | 73/8 |
| 3,367,170 | 2/1968 | Lynch et al. | 73/9 |
| 4,072,220 | * 2/1978 | Hamada | 192/0.075 |
| 4,594,878 | 6/1986 | Abe et al. | 73/9 |
| 4,662,211 | 5/1987 | Strong | 73/9 |
| 4,811,591 | 3/1989 | Antoine | 73/9 |
| 4,909,073 | 3/1990 | Takahashi et al. | 73/146 |
| 4,949,574 | 8/1990 | Linden et al. | 73/146 |
| 4,955,933 | 9/1990 | Sistonen | 73/9 |
| 5,547,034 | * 8/1996 | Wurz et al. | 73/9 |
| 5,734,088 | * 3/1998 | Gunderson | 73/9 |
| 5,746,302 | * 5/1998 | Bowman | 198/496 |
| 5,758,237 | * 5/1998 | Abramsohn | 399/249 |

* cited by examiner

Primary Examiner—Benjamin R. Fuller
Assistant Examiner—Octavia Davis
(74) Attorney, Agent, or Firm—Perman & Green, LLP

(57) ABSTRACT

Apparatus for measuring the static coefficient of friction (SCOF) of the surface of an operating conveyor belt comprises a friction roller rotatable about an axis perpendicular to the direction of movement of the conveyor belt, a friction roller actuator for moving the friction roller between a retracted disengaged position and an advanced engaged position, and a friction roller drive motor selectively operable, in one instance, for permitting free wheeling rotation of said friction roller when rotatably engaged with the conveyor belt and, in another instance, for rotating said friction roller about the friction roller axis in a direction opposite the direction of movement of the conveyor belt. A sensor continuously senses the current drawn by the friction roller drive motor and a computer is responsive to the output of the sensor when it reaches a maximum value for calculating the SCOF of the surface of the conveyor belt, the SCOF being a function of the maximum current drawn by the friction roller drive motor. Then, for cleaning the conveyor belt the apparatus comprises a brush roller rotatable about an axis perpendicular to the direction of movement of the conveyor belt, a brush roller actuator for moving the brush roller between a retracted position disengaged from the conveyor belt and an advanced position rotatably engaged with the conveyor belt, and a brush roller drive motor for rotating the brush roller about the brush roller axis when the brush roller is engaged with the conveyor belt.

29 Claims, 5 Drawing Sheets

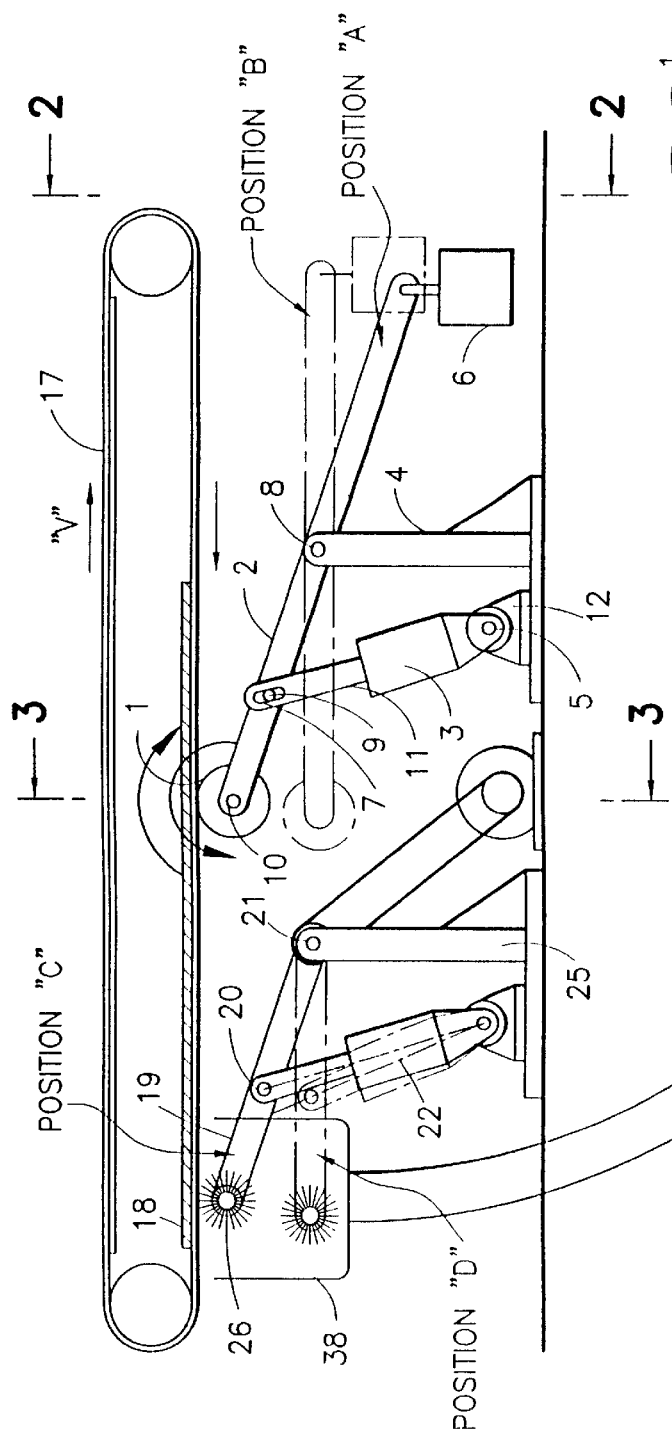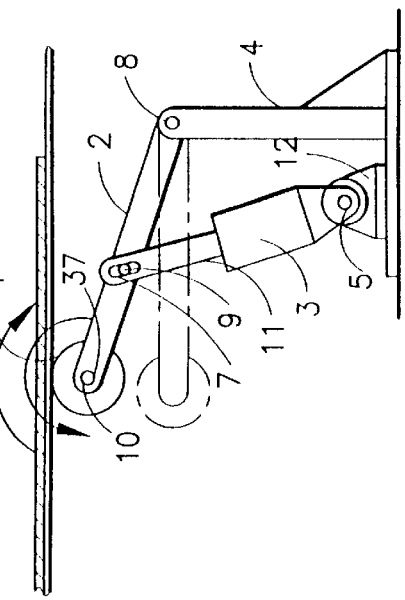

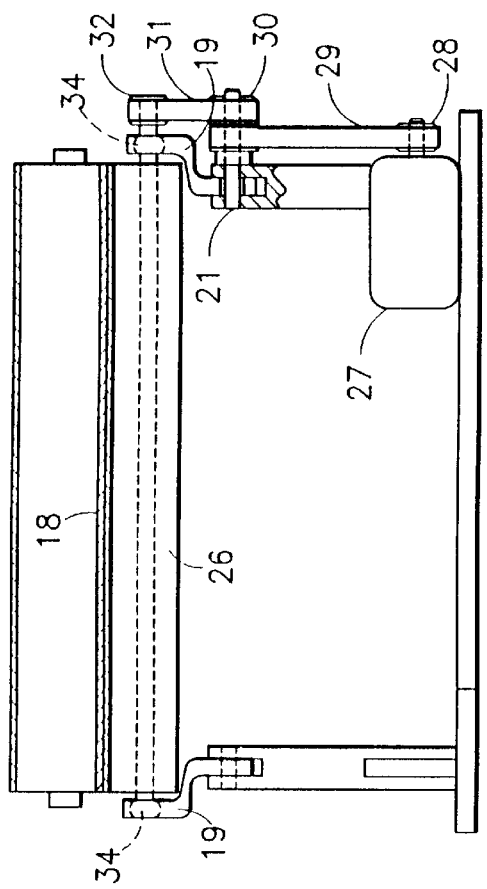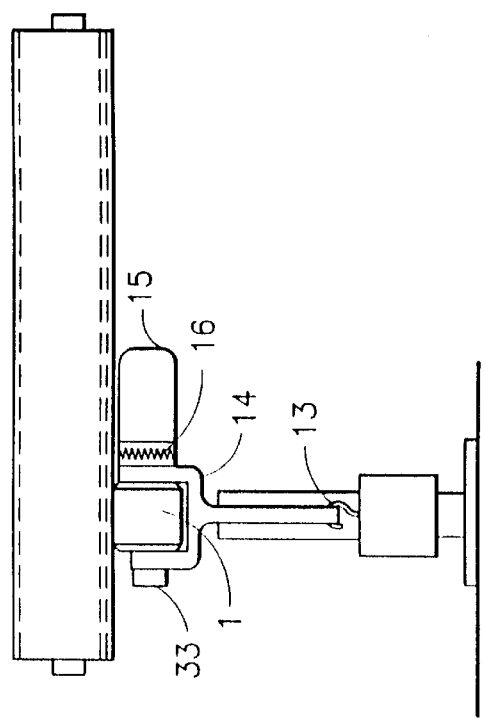

CONVEYOR FRICTION MEASUREMENT AND CLEANING SYSTEM

BACKGROUND OF THE INVENTION

1. Field of the Invention

The present invention relates generally to a device to automatically measure the static coefficient of friction (SCOF) on a moving conveyor belt and a means to initiate in-process reinstatement of the SCOF, if a reduction below the design range is detected.

2. Description of the Prior Art

The SCOF is an important parameter in the design of a certain class of machines having conveyors where obtaining necessary accelerations of conveyed parts is completely dependent only on the value of the SCOF, and also where the normal force acting on the conveyor does not exceed the weight of the conveyed part. This conveyor type will be referred to as non positive drive, with no normal force enhancement or for the purposes of discussion, a type three conveyors (A more complete discussion of conveyor types will be explained later in this disclosure)

The reason why this class of conveyor is considered in the design of postal equipment is because this configuration is relatively simple, which yields a design that is low cost and more reliable.

Since the net result of SCOF measurement will directly lead to the cleaning of the conveyor surface, it can be argued that this can be accomplished by regular maintenance procedure on the part of Postal Service personnel. Even though this improvement can be approached in this way (at least theoretically), in practice it can never be optimized when compared to an in-process determination, and also since conveyor cleaning is almost never done in postal facilities since it generally would be done at the expense of mail sorting production time.

This invention is therefore important because it can significantly improve the production efficiency of the type three conveyor, by permitting the use of SCOF values which are significantly greater than those presently being used. The in-process aspect of this procedure will also mean that valuable maintenance time need not be devoted to conveyor cleaning. The potential of a significantly greater SCOF together with the already obvious advantages of low cost and reliability can result in a significant discriminator in improving the competitive position of machines incorporating the invention.

In the design of the type three conveyor production cycle, the acceleration and deceleration portions of the cycle are developed such that selected accelerations do not exceed the value of the SCOF during initial delivery of mail to the conveyor from induction stations, during subsequent constant velocity transporting, or during the critical process of exiting from the carrier cells into the designated sort bins. The net result of not accelerating (or decelerating) the conveyor beyond the limits established by the SCOF, is that synchronismn is maintained throughout the sortation process between the conveyor and the mail being conveyed. In other words, system throughput and sort accuracy are completely dependent on the established minimum acceptable value of the SCOF.

The SCOF is normally measured statically and off-line, by either of several standard (manual) methods. In general, these manual methods are used to obtain data which are then used to define acceptable values for the SCOF, and in turn are then used as a parameter in the dynamics equations of the conveying process. In the design of the SPBS (Small Parcel And Bundle Sorter), the acceleration rates were based upon SCOF values available with new (uncontaminated) belt surfaces which then were reduced by at least 40%, in anticipation of subsequent surface contamination during mail sortation. Conveyor surface contamination is primarily due to a deposition of airborne dust and oil and also embedded debris typical in a postal mail processing facility. This reduction from the ideal value of the SCOF guarantees that synchronous operation will be maintained even in the presence of dirty belts but also results in a significant compromise from the ideal production rates possible if the conveyor belts were consistently maintained at values close to the maximum ideal available value of the SCOF. The single most important advantage of this invention is that it can substantially eliminate the need to reduce the initially higher acceleration rate available, by not permitting the conveyor belt to be significantly contaminated, and thereby realizing the advantage of higher acceleration/deceleration rates which result in proportionately greater throughput and improved sort accuracy.

An objective of this disclosure is to describe a method of SCOF measurement which would be totally automated, and in-process, being performed on a moving conveyor.

A further objective of this disclosure is to describe a method of automated SCOF measurement which is performed under dynamic conditions, as opposed to the traditional manual methods of SCOF measurement which are obtained under static equilibrium conditions. This unique difference in obtaining the value of the SCOF is the key to realizing the benefits of in-process determination of this parameter which directly lead to automated improvement in process control.

Measurement of the SCOF will be remote, using electrical transducers, whose output will be identical to the value obtained by the standard manual methods. The remote measurement of SCOF is not used to the knowledge of the applicants in any postal sorting machine. This in-process, automated scheme would yield the advantage of assessing the SCOF in an ongoing method of evaluating the process in an effort to obtain greater productivity and process control. The information will be utilized to correct the process if a small degradation in the SCOF design range is detected, and also before the process is adversely affected by such degradation. Since the value of the SCOF generally decreases due to contamination of the conveyor drive surface, any method which can dynamically measure the SCOF in-process and which can reinstate the SCOF substantially to its original design range, can significantly improve the productivity of the process. In practice the SCOF measurement obtained with new belts (completely uncontaminated) cannot be completely reinstated after cleaning due to some surface changes resulting from the cleaning process. Actual tests indicate however, that a significant increase in the SCOF is realized as a result of cleaning.

In respect to sorting machines, this benefit will be to improve throughput or sort accuracy. The objective of this disclosure is to describe a method to obtain these benefits.

The SCOF is defined here as the maximum value of the force required to move a piece of mail relative to the conveyor surface, divided by the weight of the mail. Explained in physical terms, it is the result of obtaining the threshold value of slip of the mail relative to the conveyor surface, resulting in the start of undesirable asynchronous movement of mail relative to the conveyor surface. Since this threshold value is a ratio of two forces, the SCOF is a non dimensional parameter.

In general, the acceleration/deceleration portions of the production cycle are designed such that the value of the SCOF is not exceeded since when this threshold is crossed, the dynamic coefficient of friction (DCOF) dominates and its value is significantly smaller than the SCOF. Predictions related to the arrival of mail pieces at defined positions in a sortation cycle, either in successful delivery onto carrier cells from an induction station or in successful exiting of mail into the correct sort bin are best determined under conditions of synchronous delivery. This is due to the fact that this process yields the minimum process time, and therefore, the maximum productivity.

A description of some typical conveyor types used in mail processing is helpful in identifying the specific conveyor category which will benefit the most by this-invention. In general, three types of conveyors are used to transport mail:

(1) Positive drive conveyors using cleats attached to the conveyor surface; the driving cleat provides unlimited acceleration of transported mail, but a constant pitch is required between cleats which has the disadvantage of limiting throughput with varying length packages.

(2) Conveyors which increase the normal force to a value greater than the weight force; this conveyor type also can improve the available acceleration rate substantially as with spring loaded rollers bearing down on the object during transporting, but has the disadvantage of greater complexity and cost. This conveyor type is frequently used with letter mail transporting where letter thicknesses do not vary significantly, but is impractical with packages.

(3) Conveyors which rely strictly on the SCOF for driving objects being conveyed; in this conveyor category, throughput can be maximized for any conveyor speed as compared to the category one conveyor for objects of varying length, since a variable pitch can be developed. This is the simplest conveyor type, however its main limitation is the fact that due the state of the art in conveyor materials, the available acceleration rate cannot exceed approximately 1.0. In practice, a range of only approximately 0.5 to 0.7, is available when the conveyor materials are new uncontaminated and when transporting packages covered with very slippery, and therefore, worst case, packaging materials such as DuPont TYVEK® brand artificial paper.

It can be shown that the value of the SCOF is exactly equal to coefficient of the acceleration rate available during conveyor operation. A piece of mail being transported on a conveyor at constant velocity is in static equilibrium with the conveyor surface, and is maintained in this synchronous condition by the force of friction:

$$F=(SCOF)N \quad (1)$$

where SCOF equals the static coefficient of friction, and N equals the normal force between the mail and the conveyor surface, which in the case of conveyor, three is equal to the weight force W.

The force necessary to displace the mail piece relative to the conveyor surface, is governed by Newton's second law:

$$F=(m)(a) \text{ or } F=(W/g)(a) \quad (2)$$

Equation (1) can be equated to equation (2), in order to determine the relationship between the SCOF and the acceleration rate, at the threshold between synchronous and non synchronous motion.

$$(SCOF)W=(W/g)(a) \quad (3)$$

since the weight (W) is on both sides of the equation, it will drop out, yielding the following expression:

$$SCOF(g)=a \quad (4)$$

This expression indicates that the SCOF determines the value of the acceleration rate (a), in terms of the acceleration of gravity (g), which is a universal constant equal to 386.4 in/sec/sec.

The interpretation of equation (4) is that the value of acceleration (a) that the conveyor and mail piece can be exposed to (without relative motion of the mail with respect to the conveyor surface and therefore maintaining synchronism), is equal to static coefficient of friction (SCOF) multiplied by the acceleration of gravity.

A number of patents can be cited to typify the prior art. For example, U.S. Pat. No. 4,955,933 issued Sep. 11, 1990 to Sistonen discloses a device for measuring the friction on a surface, comprising a measuring wheel and an arm attached to the wheel axle, and a spring attached between the measuring wheel and its axle. The spring is arranged to resist the rotation of the measuring wheel when the measuring wheel is moved by the arm on the surface under measurement. The arm is rigid and is provided with a straight part which is permanently attached to the axle, and at the other end thereof a pull handle is provided. The arm is provided with an inclination indicator. In the measuring position, the straight part of the arm is kept parallel to the surface under measurement. The pull handle is then kept farther away than the radius of the measuring wheel with respect to the surface and is rotatable about an axis parallel to the axle.

U.S. Pat. No. 4,949,574 issued Aug. 21, 1990 to Linden et al. discloses a testing device for vehicle tires and especially anti-skid features situated in the vehicle tire. The tire to be tested is pressed against an outer circle or surface of another tire while the two tires are rotated in opposite directions. The other tire, acting as a counterpart or pair for the tire being tested, is a pneumatic tire, while the tire to be tested and the other tire are disposed to be pressed against one another so that a contact surface between the two tires is substantially straight. The other tire acting as the pair or counterpart for the tire to be tested is provided with a wear surface having good wear resistance properties.

U.S. Pat. No. 4,909,073 issued Mar. 20, 1990 to Takahashi et al. discloses apparatus for measuring a resistance against slippage on the road surface. The apparatus is so constructed that two measuring wheels adapted to be rotated by imparting a tractive force to the apparatus are connected to one another via a torsion bar extending between them. A difference in rotation is forcibly produced by changing the rotational speed of one of the measuring wheels and a slippage resistance on the road surface is measured by detecting a torque generated on the torsion bar due to the slippage resistance on the road surface.

U.S. Pat. No. 4,811,591 issued Mar. 14, 1989 to Antoine discloses a device for checking the surface condition of a material. The device is essentially comprised of an adherence measuring sensor whose sensitive element is set in contact with the surface of the material while in relative motion with respect to the surface. An associated computer provides for the comparative measurement, the display and the possible piloting of the surface treatment or production apparatus. The sensor comprises two wheels mounted on fluid bearings and rolling on the material of which the surface condition is to be controlled and devices for measuring the speed differential of the wheels and providing for the progressive braking of one of the wheels.

U.S. Pat. No. 4,662,211 issued May 5, 1987 to Strong discloses a wheeled vehicle constructed to be propelled along a test surface in a predetermined direction. A test wheel assembly includes a test wheel carried by a hub to rotate about an axis perpendicular to the direction of vehicle travel, with transducers being mounted on the hub and coupled to the test wheel for dynamically measuring forces acting on the test wheel horizontally in the direction of travel and vertically perpendicular to the direction of travel. A drive mechanism is coupled to at least one wheel of the vehicle and to the test wheel for driving the test wheel at predetermined slip with respect to the vehicle wheel. An important feature resides in the construction according to which the drive mechanism is suspended from the vehicle frame and held against rotation about the axis of the vehicle wheel coupled thereto, and the test wheel transducer is suspended from the drive mechanism and held against rotation with respect to the test wheel axis. In this way, transducer orientation is maintained independently of undulations in the test surface.

U.S. Pat. No. 4,594,878 issued Jun. 17, 1986 to Abe et al. discloses a dynamic friction coefficient measuring apparatus. It includes a friction measuring portion having a disc with a friction measuring rubber member attached thereto, a driving disc adapted to rotate coaxially with the disc and a dynamometer which interconnects the disc and the driving disc. A tachometer measures the speed of the rubber member during rotation of the friction measuring portion. An X-Y recorder records two electric outputs of the friction measuring portion and the tachometer onto rectangular coordinates.

As disclosed in U.S. Pat. No. 3,367,170 issued Feb. 6, 1968 to Lynch et al., to measure the coefficient of friction of a surface, a body having a shiftable center of gravity is pulled or pushed along the surface. A scale is attached to the body. When the center of gravity has shifted enough to create a restoring force equal to the moment introduced by the friction force, the reading on the scale at that instant is the coefficient of friction of the surface.

U.S. Pat. No. 3,152,468 issued Oct. 13, 1964 to Powell discloses a tire testing system wherein a drive shaft rotates a drive gear and a tire-driving drum. A tire in engagement with the drum is connected by a shaft to a side gear of a differential. The other side gear of the differential is connected to a spur gear connected through an idler gear to the drive gear. The rear ratio of the drive gear to the spur gear is equal to the diameter ratio of the drum and the tire so that the ring gear of the differential normally remains stationary, regardless of the speed of the tire. By urging the ring gear in one direction the tire is subjected to braking forces. Rotation of the ring gear in the other direction subjects the tire to acceleration forces.

U.S. Pat. No. 2,990,713 issued Jul. 4, 1961 to Heffelfinger et al. discloses apparatus which relates to the measurement of the frictional properties of various materials, and is especially useful in determining the inter-fiber dynamic and static frictional properties and stick-slip characteristics of textile fibers. Fundamentally, the invention operates on the principle of a brake band, and in practice the sample under test is composed of two parts which are pressed together with a known pressure and moved relative to each other. In effect, the two sample parts represent a brake drum and belt, and the resistance to the movement of the parts relative to each other is measured and recorded.

It was with knowledge of the foregoing state of the technology that the present, invention has been conceived and is now reduced to practice. The concept embodied by this invention is different from all of the devices reviewed above. Specifically, none of the patents found in the search disclose measuring the current of the motor, especially the maximum current of the motor, in order to determine coefficient of friction. Furthermore, the patents relating to aircraft wheels are not applicable to conveyor belts because of differences in the surfaces. An aircraft tire is subjected to relatively hard impacts with the runway, resulting in removal of some of the tread of the tire and thus renewing the contacting or working surface of the tire. In contrast, mail pieces land on a postal conveyor relatively and very desirably so as to avoid damage, softly. For this reason, the conveyor surface would not be renewed as would that of an aircraft tire. The scope of the invention is broad enough to consider using an intermediate layer of the "worst-case" mail piece external material, TYVEK® brand artificial paper, to make the coefficient of friction measurements. Also, within the scope of the invention is making the roller of highly polished or hardened steel. A soft roller would tend to receive foreign substances more readily than would a roller of hard material and thus would produce variations in its surface and would vary the coefficient of friction being measured.

SUMMARY OF THE INVENTION

The present invention relates to apparatus for measuring the static coefficient of friction (SCOF) of the surface of an operating conveyor belt comprises a friction roller rotatable about an axis perpendicular to the direction of movement of the conveyor belt, a friction roller actuator for moving the friction roller between a retracted disengaged position and an advanced engaged position, and a friction roller drive motor selectively operable, in one instance, for permitting free wheeling rotation of said friction roller when rotatably engaged with the conveyor belt and, in another instance, for rotating said friction roller about the friction roller axis in a direction opposite the direction of movement of the conveyor belt. A sensor continuously senses the current drawn by the friction roller drive motor and a computer is responsive to the output of the sensor when it reaches a maximum value for calculating the SCOF of the surface of the conveyor belt, the SCOF being a function of the maximum current drawn by the friction roller drive motor. Then, for cleaning the conveyor belt the apparatus comprises a brush roller rotatable about an axis perpendicular to the direction of movement of the conveyor belt, a brush roller actuator for moving the brush roller between a retracted position disengaged from the conveyor belt and an advanced position rotatably engaged with the conveyor belt, and a brush roller drive motor for rotating the brush roller about the brush roller axis when the brush roller is engaged with the conveyor belt.

The following features are present in this disclosure:
(1) a conveyor friction measurement and cleaning system:
  (a) which can measure the SCOF and DCOF automatically and in-process on moving conveyors;
  (b) which can automatically clean contaminated conveyors in-process, based on data received from the friction measurement unit;
  (c) which can automatically reinstate the original SCOF and DCOF of the belt when combined with any packaging material such as TYVEK® brand material. This reinstatement is performed with abrasive brushes which remove accumulated contaminants on the belt surface, and a small amount of belting material;
  (d) which provides just enough cleaning to minimize the belt wear resulting from the process. This is accomplished by simultaneously measuring the SCOF, during the process of cleaning;

(e) which can detect a "worn out" belt by monitoring the length of time to complete the operation, and stopping the process after a predetermined time interval is reached;

(f) which determines the SCOF based on the magnitude of the motor current required to obtain the threshold of slip between a motor driven roller and the belt surface. The rotation of the roller can be either in the opposite direction to belt motion or in the same direction as belt motion;

(g) which can measure the DCOF, based on the magnitude of the continuous slip current, after the peak SCOF measurement is made;

(h) system which is initiated by a timer that starts the process based on the information related to the contamination level expected at each mail processing facility; and (i) which determines the SCOF values using a calculator (or computer), and initiates the cleaning cycle based on selecting appropriate SCOF values to maximize the time between cleaning cycles;

(2) a friction measurement unit:
(a) which uses a strain gauge to measure the normal force, to automatically account for long term variations in the measurement process;
(b) which can also use a weight to apply normal forces during the process;
(c) which engages the moving conveyor belt by using a linear actuator, which transfers the force application to a weight by using a slotted pivot arm. A hook is used to consistently obtain a vertical acting force;
(d) which also can use a strain gauge to measure actual developed normal force, and can use this value to determine the SCOF and DCOF of the belt. The developed force in the actuator is used directly to apply force to the actuator, by a direct connection to the driving pin;
(e) which uses an electrically actuated clutch to disengage the motor armature inertia during initial contact with the belt, in order to minimize the stabilization time; and
(f) which uses a tachometer to determine the velocity of the friction roller, in order to minimize the time, and to initiate the motor starting function; and (3) a belt cleaning unit:
(a) which uses air actuated cylinders to apply a high level of force to the brush during the cleaning operation. The cylinder motion applies a consistent force and automatically adapts to brush wear;
(b) where the ail cylinders can apply variable forces if required to loosen embedded contamination;
(c) which uses a stationary motor to drive the cleaning roller, which is mounted on a moving pivot arm;
(d) which utilizes two self aligning bearings to support the cleaning roller in such a way that provides for constant pressure along the full width of the cleaning area. This is done through the process of coupling the air cylinders to apply pressure independently through each spherical bearing; and
(e) which removes debris created in the cleaning process, by using a vacuum removal system which is activated at the start of the cleaning process.

Other and further features, advantages, and benefits of the invention will become apparent in the following description taken in conjunction with the following drawings. It is to be understood that the foregoing general description and the following detailed description are exemplary and explanatory but are not to be restrictive of the invention. The accompanying drawings which are incorporated in and constitute a part of this invention, illustrate one of the embodiments of the invention, and together with the description, serve to explain the principles of the invention in general terms. Like numerals refer to like parts throughout the disclosure.

BRIEF DESCRIPTION OF THE DRAWINGS

FIG. 1 is a side elevation view, partly in section, diagrammatically illustrating a conveyor friction measurement and cleaning system embodying the present invention;

FIG. 1A is a detail side elevation view of a portion of FIG. 1 illustrating another embodiment of the invention;

FIG. 2 is an end elevation view of the system illustrated in FIG. 1 and taken generally along line 2—2 in FIG. 1;

FIG. 3 is a detail sectional view taken generally along line 3—3 in FIG. 1;

DETAILED DESCRIPTION OF THE PREFERRED EMBODIMENTS

Figure 4:
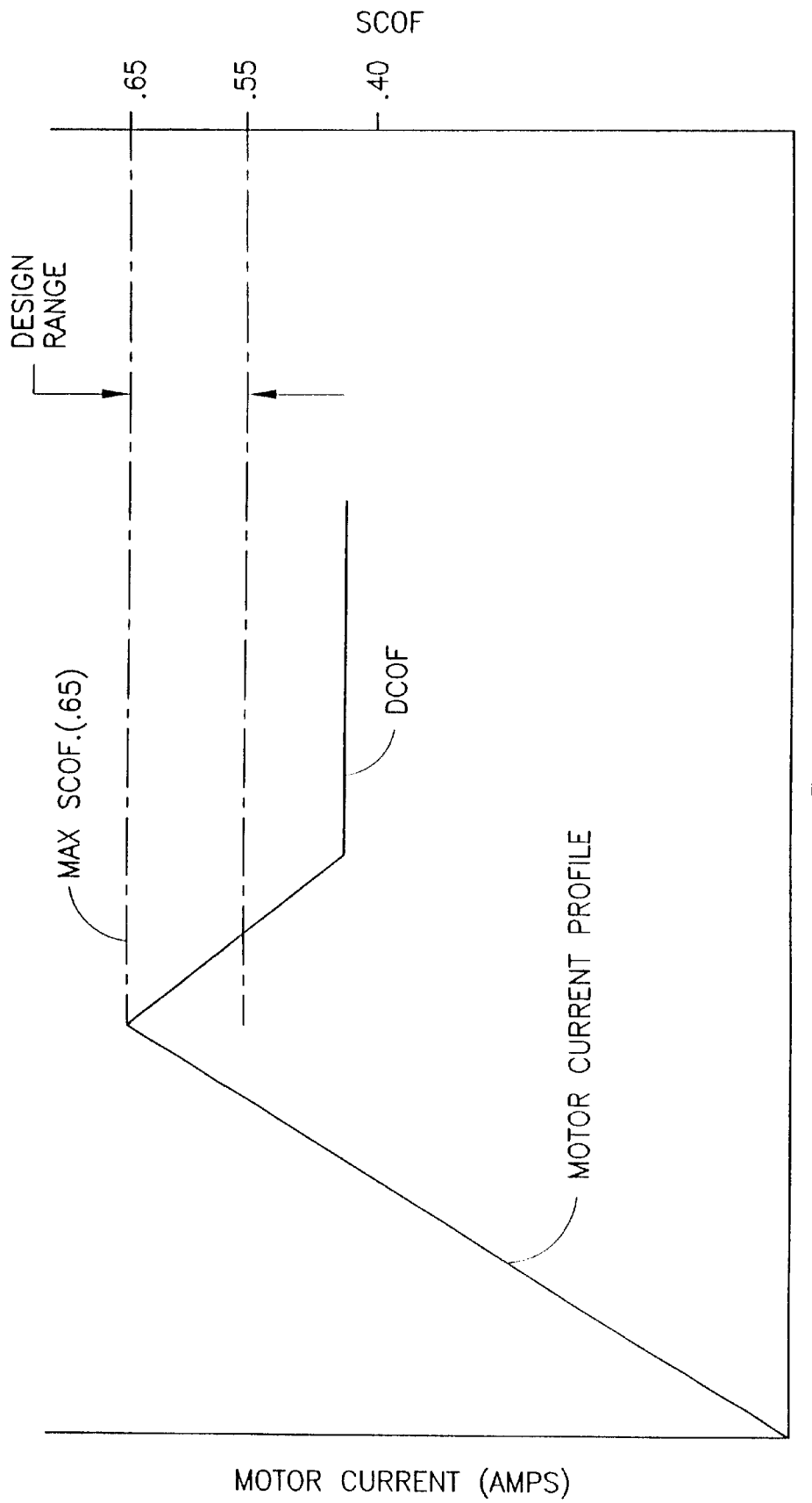
FIG. 4 is a graph displaying electrical current drawn by the motor for driving the friction roller versus time.

Discussion on the Importance of the SCOF and the DCOF

The SCOF is defined here as the maximum value of normal force (weight of an object) divided into the force required to move the object relative to the moving conveyor surface. Explained in physical terms it is the result of obtaining the threshold value of slip of the object relative to the conveyor surface, or obtaining the start of asynchronous movement. Since this threshold value is a ratio of two forces, the SCOF is a non dimensional parameter.

The SCOF is normally measured statically and off-line, by either of several standard (manual) methods. In general, these manual methods are used to obtain data which are then used to define acceptable values for the SCOF, and in turn are then used as parameters in the dynamics equations of the conveying process.

The Static Coefficient Of Friction (SCOF) is an important parameter in the design of many machines, since transporting product in some types of machines either at constant velocity, or during acceleration/deceleration sequences, can be completely dependent on maintaining the SCOF at certain predetermined design values. Failure to maintain the predetermined value of SCOF generally results in synchronism loss which in turn leads to decreasing process productivity.

In general, the acceleration/deceleration portions of the production cycle are designed such that the value of the SCOF is not exceeded since when this threshold is crossed, the dynamic coefficient of friction (DCOF) dominates and its value is significantly smaller than the SCOF. The lower DCOF value will increase processing time and reduce accuracy proportionately.

Relationship of the SCOF to the Maximum Usable Acceleration/Deceleration Rate

It can be shown that the value of the SCOF is exactly equal to the acceleration rate available during synchronous conveyor motion. The purpose of verifying this relationship is that it validates the importance of measuring the SCOF as being directly representative of the acceleration rate available from conveyor surfaces. Also. it identifies those parameters which must be measured to obtain the value of the SCOF. These parameters are the friction force and the normal force. The value of Friction Force=SCOF×N, can be equated to the Acceleration Force=M×A (Newton's second law). Since M=W/g, and also since N=W, the weight parameter cancels out leaving SCOF=A/g. The value of SCOF therefore is a constant, since both A and g have the units of acceleration (in/sec/sec).

Also, rearranging this expression yields: A=g·(SCOF). which indicates that the available acceleration rate is equal to a constant multiplied by the acceleration of gravity. Essentially, this verifies that the SCOF is directly related to the available acceleration rate. This fact highlights the importance of the invention, since it identifies a convenient parameter which can be measured (SCOF), which is a reflection of the available acceleration rate of the conveyor surface.

Mathematical Basis of the Invention

The mathematical expression for friction force will be used to identify those parameters which need to be measured and calculated automatically, in order to be able to determine the value of the SCOF of conveyor surfaces. The friction force equation can be expressed as F=(N)·SCOF. Or by rearranging, and solving for SCOF, one can obtain SCOF= F/N. Therefore, if the friction force (F) can be measured and the normal force (N) can be measured, then the SCOF can be calculated. This is the method used in this disclosure to configure the device.

As will be explained in greater detail later, the friction force is conveniently measured by electrically measuring the value of motor current and relating this value to the required friction force. Likewise, the normal force is also measured by either an electrical indication using a strain gauge, or by using an equal arm balance. Finally, once these values are obtained, the data is then used to calculate the SCOF. At this stage, the motor current correction factors can be introduced which can account for bearing friction and windage resistance, and other factors, in order to refine the calculations.

Importance of the SCOF Measuring Device

The SCOF detection device is of particular benefit in the general category of machine where packages are transported with normal forces which are created by the weight force of the package. The present Small Parcel And Bundle Sorter (SPBS), and the Small Footprint Parcel Sorter (SFPS), are examples of this category of machine. Also, the FSM 1000 falls into this category since static driving friction forces are used to transport mail. The effect of belt contamination in this system, may be less however, since the vertical side wall belts may be sharing the acceleration load. Extended operation of this system in a USPS postal environment may also surface the same problems as already evidenced on SPBS.

Major Benefits in Mail Processing Applications

The major benefits of this disclosure are that the methods described provide for the SCOF and DCOF to be measured automatically, with no manual assistance and with low maintenance. This means that the information obtained can be used to modify conveyor surface frictional properties, also automatically. The operating devices can be remotely located, as a result of these features. Additional features also provide for measurement and cleaning to take place in-process, or during actual processing of mall.

Conveyor Friction Measurement and Cleaning System

This disclosure addresses the problem of conveyor belt surface friction degradation (and its effect on productivity loss in sorting machines), together with a means of restoring conveyor belt frictional properties, which have been degraded. In this implementation, both the measurement device and the cleaning means are discussed as a system which has special advantages in automatically detecting loss of surface friction properties during an in-process evaluation, and also automatically initiating an in-process cleaning cycle (if required) based on assessment of measurement data. Also, a new belt cleaning device will be discussed, which has unique features not present in the patents reviewed in this area. The cleaning cycle would then reinstate the belt surface frictional properties to their original design range.

I believe that the discussion of the Measurement And Cleaning System, which also includes information needed for the standalone Coefficient Of Friction and Belt Cleaning Devices, have the most commercial benefit and therefore will be described first. A description of the last device, will be submitted at a later date.

Background of the Conveyor Surface Degradation Problem

An important insight into the nature of the conveyor surface degradation problem was made by comparing this conveying means with the example of automobile tires, winch was the subject of discussion on some of the coefficient of friction patents reviewed during this investigation.

Both conveyors and automobile tires have the same objective, which is to move objects or materials from one place to the next. The fundamental difference between these applications is that tires continuously wear, and therefore continually expose virgin rubber surfaces to contact the road. Continuous wear of tire surfaces results in preserving the tire frictional properties since a (coefficient lowering) layer of contamination is not allowed to deposit on the tire surface. As a result, the original predicted design ranges of the SCOF (between the tire and the road surface) can be relied upon. This process is aided by two factors:

(a) Acceleration and deceleration of the tires frequently creates relative motion or "slip" during use.

(b) A very high unit pressure loading between the tire and the road which can be at least 100 times as great as that experienced in typical mail handling conveyors.

By comparison, in mail sorting conveyors, the opposite conditions exist, since the original (maximum value) SCOF of new belt surfaces is not renewed in service due to the almost complete absence of conveyor surface wear. The net result is that ever present surface contamination gradually leads to reducing the coefficient of friction to a value which is approximately 30% lower than that available from new belts. The reasons for these conditions are listed below:

(c) In general, mail sorting conveyors are designed to run synchronously as much as possible since in most cases a loss of synchronism results in mail missorts or a loss in system throughput, therefore, little (if any) slip takes place by design.

Synchronous conditions do not lead to slip and therefore do not normally create the relative motion necessary for wear to take place. If wear does not take place, then conveyor surfaces will not continuously "renew" their driving surfaces, as is the case with auto tires. Lack of renewal of the conveyor surface sets the stage for a gradual accumulation of contaminants, which are present in the form of airborne oil particles, paper dust, and marking ink, from packages being transported. In addition, with respect to some type of conveyors, the contaminants are embedded into the conveyor surface, by a high unit loading of "pinch rollers" (installed to obtain synchronous operation) which tend to quickly make the contaminant layer an ingrained part of the conveyor surface, further aggravating the problem.

(d) Mail sorting conveyors are exposed to very low unit pressures during use, which can be much less than one pound per square inch.

This further aggravates the problem of not renewing the conveyor belt surface, since the much reduced unit force is not as prone to abrading the conveyor surface, even if relative motion does take place.

The primary conclusion to be drawn from the above analysis, is that most mail handling conveyors of the straight ("gravity only" normal force type) do not wear out, but rather are replaced due to tearing, edge contact wear (due to belt mistracking) or because they look dirty. This has been verified by examining conveyor belts which have been returned to the manufacturer from the Postal Service during the warranty phase of the SPBS program. This conclusion highlights the fact that in general, the loss of performance in mail transport conveyors due to degradation in the SCOF is a problem unique to mail sorting conveyors, and still remains to be solved. The class of conveyors referred to here are those where the weight force is the only contributor to the normal force, and therefore is the only contributor to the available acceleration rate.

The second conclusion is that under normal circumstances, frictional properties are highest when the belt is new and gradually degrade as a function of machine mail processing time, due to accumulated contamination on conveying surfaces. The process appears to stabilize at a level which is a)proximately 40% lower than that available when the belt is new. The contaminated surface essentially creates a new (stabilized) lower SCOF level when measured against the worst case packaging material. The worst case standard of reference in mail sorting machines is the SCOF of Dupont TYVEK® brand material, when measured in contact with low (35) durometer PVC belting material. This is an important parameter since it establishes the throughput capability of the mail sorting machine, by establishing the design acceleration rate of packages being conveyed. A realistic average value of the worst case SCOF is approximately 0.65, when the PVC belts are uncontaminated and in a "new" condition.

As a point of information, normal maintenance procedures call for periodic (manual) belt cleaning, but this is seldom done because of lack of maintenance time.

Periodic manual belt cleaning would solve the problem of maintaining the original value of the SCOF and, as such, would permit using the higher value instead of the present approach of using the degraded value, but the problem is that it is not being performed due to lack of maintenance time and also since it is time consuming manual labor and therefore is costly. Also, belt cleaning must be performed "off line", or at a time when the machine is idle and not processing mail.

This highlights one important advantage of automatic "in-process" cleaning, since it would not require costly maintenance time, and also in most cases would not require machine shutdown to complete.

The Net Benefit of the System Described in this Disclosure (1) Mail sorting machine throughput can be increased by at least 25%, by detecting belt friction degradation and automatically cleaning the conveyor belts as required, to restore the belt surface to substantially new condition.

The net result is that higher (uncontaminated) belt SCOF values can be used to establish the machine cycle times which in turn results in proportionately higher system throughput. Utilizing the higher SCOF value, (available when belts are cleaned to a substantially new condition) can directly lead to an increase in correctly sorted throughput by at least 25%, when sorting worst case (TYVEK® brand) mail pieces.

(2) Since the detection and cleaning process takes place on the underside (return path) of the belt, it can be performed in-process (during mail sortation, in most cases), and therefore would not require costly manpower to accomplish. Also, (in most cases) the machine would not require a shutdown period to clean the belts, which would improve machine "up time" productivity. In this position, the detection and cleaning devices do not interfere with normal mail conveying, which takes place on the top surface of the conveyor belt.

In those cases where the belts cannot be cleaned in-process, the cleaning can still take place automatically, and therefore without costly manual labor.

(3) A (less desirable) alternate approach to measuring the SCOF, and using this data to initiate belt cleaning, would be to operate the belt cleaning system in continuous contact with the conveyor belt. This method would keep the belt free of contamination, but would also lead to premature wear, since cleaning would take place when it is not required. Abrasive (dry) brushes will be required with the new cleaning approach, to remove embedded contamination with a relatively high contact force. Therefore, the time of contact of these brushes with the conveyor belt surface will need to be minimized in order to optimize the life of the belt.

Therefore, another benefit of the detection portion of this system is that it would optimize the useful life of the conveyor belt, by cleaning the belt only when required.

(4) As standalone devices, the SCOF and DCOF measurement devices, have uses other than those mentioned here, which are primarily related to conveyors.

Description of Conveyor Friction Measurement and Cleaning System

FIG. 1 illustrates the Conveyor Friction Measurement And Cleaning System shown in position on the underside of a typical mail sorting conveyor. Mail is transported on the top surface of the conveyor, and the return path on the bottom of the conveyor is used as a convenient location to measure the friction properties of the belt material, and to also clean the belt. As indicated in FIG. 1, the right hand device is the Friction Measurement Unit, while the device on the left is the Belt Cleaning Unit.

Both of these units operate in essentially two modes:

(a) The Conveyor Friction Measurement Unit, is either in position "B", (or disconnected) and with its friction measurement roller not in contact with the conveyor belt, or in position "A", with the friction roller in contact with the belt during the measurement cycle.

(b) The Belt Cleaning Unit also is either disconnected in position "D", or in position "C", with its cleaning brush in contact with the belt.

The belt cleaning unit can be engaged while the belt measuring unit is disengaged, and vise versa.

Sequence of Operation of the Measurement and Cleaning System (1) Both the Measurement and Cleaning Units are initially disconnected, and therefore are not in contact with the conveyor belt.

(2) The Friction Measurement Unit is the first to be automatically activated, at some defined frequency, based on the rate (to be determined) of belt contamination at each facility.

(3) Data is obtained from the Friction Measurement Unit, which is then compared to the established design SCOF range of the conveyor belt in the system. This range used would be typical for a belt transporting TYVEK® brand packages. The mail processing belts are made from low durometer PVC, and the SCOF design range could be between about 0.55 to about 0.65. FIG. 4 shows a typical SCOF design range, where the top part of the range is coincident with the maximum expected SCOF value of about 0.65. The design value of the SCOF range is established to satisfy the acceleration requirements of the sorting belts that determine machine cycle times.

(4) If the data obtained indicates that the measured SCOF has drifted into the lowest quarter of the range, the cleaning unit is then actuated to remove the accumulated contamination on the belt surface.

(5) During the course of the cleaning cycle, the Friction Measurement Unit is initially disengaged, but is periodically reengaged, during the cleaning cycle in order to continually assess the improving frictional properties of the conveyor belt surface, as contamination is removed. This may occur several times during the course of cleaning.

(6) The Belt Cleaning Unit is disengaged when the Friction Measurement Unit records a value which is in the highest quarter (for example from about 0.63 to about 0.65, see FIG. 4) of the established design range. The relatively large range between 0.55 and 0.65 assures that there would be a reasonable time between measurement and cleaning cycles, and the frequency between cycles would be a minimum.

(7) When the target friction value within the design range is reached, both units are then disconnected, and essentially wait for the next measurement cycle to take place, based on the established frequency mentioned earlier.

Detailed Description of Operation

The Friction Measurement Unit is basically composed of a motor driven friction roller 1, which is brought into contact with the lower belt surface, as required to measure the friction condition of the conveyor belt surface. The belt is moving at a velocity "V" (see FIG. 1). The belt is supported by a backup plate 18 which provides a firm, flat reference surface for the flexible belt. The motor drives the roller through an electrically actuated tooth clutch 16 (FIG. 2), which is initially disconnected and therefore allows the roller to free wheel (counter clockwise, see FIG. 1) when first contacting the belt. Free wheeling of the roller continues until the roller accelerates to the surface velocity of the belt. The purpose of the clutch is to disengage the motor armature inertia from the roller inertia during engagement with the conveyor belt, in order to stabilize the rotational movement of the roller and to reduce the acceleration time, just prior to taking the friction measurement. At the instant when the roller velocity matches the belt velocity, the clutch is electrically engaged and the motor is powered in the reverse (clockwise) direction until slip occurs between the belt and the roller. A tachometer 33 (FIG. 2), connected to the end of the friction roller, is used to verify that the friction roller has reached the velocity of the conveyor belt surface. A simple time delay can also be used and, in this instance, reference numeral 33 may represent a timer.

Figure 5:
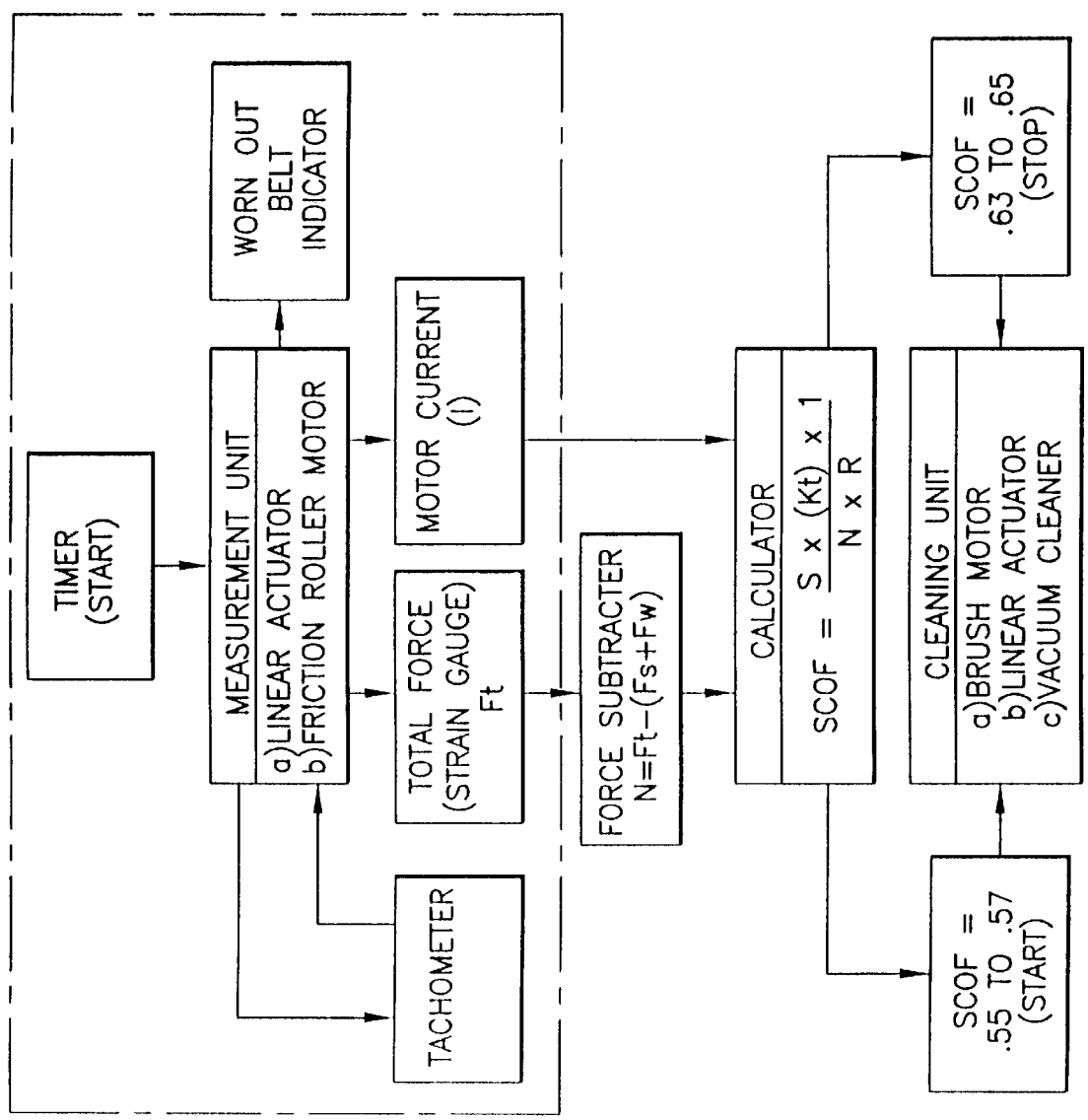
FIG. 5 is a system block diagram describing the operation of the system of the invention.

The motor current increases until sufficient torque is developed to make the roller slip relative to the belt surface. The maximum current drawn by the motor, which occurs at the threshold of slip, is measured and its magnitude is entered into the calculation of the SCOF (FIGS. 4 and 5).

Relation of Motor Current to Developed Torque

In general, the torque developed by an electric motor has a definite relationship to the current supplied to the motor. This relationship takes somewhat different forms for the various types of motors, and exhibits varying degrees of linearity. It takes its simplest form when applied to the brush-type, permanent-magnet-field, DC motor, for which torque developed is a very nearly linear function of armature current over a wide range of load conditions. For this reason, and because the such motors are easily obtained, supplied with power, and controlled, the following discussion is based on the use of a brush-type, permanent magnet motor. It should be understood, however, that other types of motors could be used if the torque characteristics thereof are suitably characterized and appropriate control means are employed.

Although the chosen motor type has a well-behaved and generally linear torque/current relationship, certain limitations do apply. An obvious and easily corrected error arises from the no-load mechanical and electrical losses internal to the motor. This correction is the subject of the present discussion, and is easily extended to include the additional mechanical losses of the remainder of the test system roller bearings, belts, and the like. Other more subtle effects occur at very heavy loads, as the reaction field produced by the armature alters the parameters of the magnetic structure of the motor and influences torque production. Fortunately, armature-reaction effects can be minimized by limiting the normal force applied to the test roller to a value that does not heavily load the motor. The motor no-load losses can be combined with the rest of the test system losses, and measured and accounted for by the procedure described below.

The motor torque constant. $K_t$, is expressed as torque/unit current, typically oz-in/amp (small motors) or lb-ft/amp (large motors). The manufacturer's rating will be accurate enough for most purposes.

Need for Current Correction Factor

The use of motor current to measure torque in a friction coefficient measuring device requires the inclusion of a correction factor which accounts for the current due to other causes which exist in any practical system. These are both electrical and mechanical in nature: the electrical causes are magnetic hysteresis and eddy current loss in the armature core, and the mechanical causes are windage (air resistance) and bearing resistance frictional and viscous in the motor and other rotating members of the test assembly.

Measurement of the correction factor is a simple matter of running the motor and test roller assembly (at the test speed) under no load conditions and reading the current. This is conveniently done at the start of a test, since it is desirable to begin the test with the motor at speed (i.e., with the test roller peripheral velocity matching the belt speed) before any normal force is applied. Running the system at a speed near that needed to match the linear velocity of the belt to be tested aids in establishing the non-slip condition needed before reversing the sense of motor current (or increasing its initial value) in order to make the frictional coefficient measurement.

The only effect not taken into account by the no-load current measurement is that of additional friction in the roller bearings due to application of the normal force used in the test. If the roller is equipped with good-quality ball bearings, this frictional force will be negligible in comparison to the other effects. It may be approximated on the basis of the bearing manufacturer's data and a corresponding current increment (based on $K_t$) may be included, if so desired.

Application of Current Correction Factor

When the test roller is engaged with the belt under test, the normal force is applied, and the roller is running in synchronism with the belt, a reduction in the motor current causes torque to be applied by the belt to the roller and motor. If the motor current is reduced to zero, the torque supplied to the roller by the belt equals that produced by the motor during the no load test (with the assumption made in the immediately preceding paragraph). If the motor current is then caused to reverse in polarity, the total torque that must be supplied to the roller by the belt is the sum of the zero-current torque and the torque developed by the reverse current. Therefore, the current correction factor must be added to the observed current.

If, on the other hand, the motor current is increased beyond the value necessary to match the belt speed and in the same polarity sense, the retarding torque supplied by the belt is equal to the incremental torque corresponding to the incremental increase in motor current. In this case, the current correction factor must be subtracted from the total observed motor current.

Current Correction Factor for a Non-Moving Belt

When the test is conducted on a stationary belt, a somewhat different approach is needed for determining the current correction factor. With the test roller not in contact with the belt, the voltage applied to the motor is increased slowly until rotation just begins. The current at this point then represents the torque which must be applied to overcome friction in the motor/test roller assembly. The other mechanical and electrical losses are negligible due to the low rotational speed.

The beginning of rotation can be sensed by a tachometer or by observing the behavior of the motor current as voltage is applied. The current will increase in proportion to the voltage until rotation begins; it will then remain nearly constant as the voltage continues to increase, because the back EMF generated by the rotation will oppose the applied voltage. Thus, the sudden change of the current behavior provides a convenient indication that rotation has begun.

After the correction factor has been determined, voltage is removed from motor and the rotating parts are allowed to come to a halt. The test roller is then engaged with the belt to be tested and the normal force is applied. The motor voltage (and current) is then increased until the current suddenly drops to a lower value as slippage begins. As in the moving-belt case, the peak current (with correction) relates to the static coefficient of friction, and the lower value relates to the dynamic coefficient.

In contrast to the moving-belt case, the torque available to rotate the roller against the stationary belt is smaller than that developed by the motor current. The correction factor must therefore be subtracted from rather than added to the observed current.

In both the moving-belt and stationary cases, it is desirable to establish a value for the correction factor before each measurement. The need for matching the moving belt speed by pre-rotation of the test assembly provides a convenient point for the correction factor measurement without adding an extra step to the moving-belt procedure. For the stationary case, a step dedicated to the correction factor measurement must be added.

Note on Voltage/Current Control for the Test Motor

The discussion thus far has referred to the control of motor speed and current without regard to the method(s) used to attain the desired values of each. These can be attained in several ways in the case of the brush-type DC motor alone, and by many additional methods if other motor types are admitted. The present discussion will be confined to the simplest example of open-loop control for a brush-type motor, but it must be understood that the use of more sophisticated control methods do not in any way alter the basis of the measurement.

The equivalent circuit of a permanent-magnet field, brush type DC motor is known to consist of a voltage source representing the back EMF, with a constant $K_b$, typically expressed in volts/rpm. This voltage source is in series with a resistor representing the resistance of the armature winding, and, in the practical sense, also including a linear approximation to other stray electrical losses which are a function of armature current. In a typical motor, the series resistance is small enough so that the corresponding voltage drop under normal operating conditions much less than the back EMF; that is, to a first approximation the motor is a constant speed device if the applied voltage is constant. Thus, the process of matching the belt speed is readily accomplished by simply increasing the voltage applied to the motor until the desired speed is attained.

After the roller has been synchronized with the belt, the situation changes. Now, the object is to control the motor torque rather than the speed, since the latter is fixed by the belt speed (in the absence of slippage). As noted above, the torque is proportional to the armature current, which is a rather sensitive function of the difference between the back EMF and the applied voltage, due to the low armature resistance. Thus, while it is possible to simply lower or raise the voltage until slippage occurs, and to measure the value of current at the onset of slippage, the voltage adjustment may be unduly critical if the motor has low armature resistance.

The critical adjustment can be circumvented by adding supplemental resistance to the circuit, so that a larger voltage change is necessary to produce the slippage torque. If the resistance is simply inserted without changing the applied voltage, the torque produced by the motor will drop and the belt under test will supply torque to the roller in order to maintain synchronism. The voltage may then be adjusted until slip occurs, while monitoring the current. If the coefficient of friction is very low, it is possible that insertion of the resistance will produce slip. In this case, it will be necessary to substitute a lower resistance, or to gradually increase the resistance from zero until slip occurs.

An alternate approach is to change the power supply from the constant voltage mode to the constant current mode. Many commercial power supplies have this capability; the constant current mode implies an infinitely high source resistance, without the attendant internal power loss.

In the non-moving belt case, the speed adjustment aspect is absent, and the motor current is the only parameter which needs to be controlled. Thus, it is logical to conduct the entire process with supplemental resistance or with a current-mode power supply.

The following is a mathematical derivation of the SCOF, based on an electromechanical torque balance.

Derivation of the Mathematical Expression for the SCOF

In order to measure the SCOF using the motor current as a measurement variable, the expression for the SCOF will be derived in terms of motor current. This is done by equating motor torque to mechanical torque generated in the measurement process.

(1) Mechanical torque $T = N \times SCOF \times R$ (2) Motor torque $= T = (K_t) I$ (3) $(K_t) \times I = N \times SCOF \times R$ or (4) $SCOF = (K_t) \times I / N \times R$ (5) When the SCOF is measured in the Measurement And Cleaning System, a scaling factor is used to reduce the value obtained for a steel roller, to make it equivalent to a TYVEK® brand coated roller. The scaling factor is determined experimentally, by performing SCOF tests on both steel and TYVEK® brand material in combination with polyvinyl chloride (PVC) belting material. The following equation includes the scaling factor;

$$SCOF = S \times (K_t) \times I / N \times R$$

(6) Definition of terms are shown below:
SCOF=Static Coefficient Of Friction (dimensionless)
R=Roller radius (feet)
N=Roller Normal force (lbs)
I=Motor Current (Amperes)
$K_t$=Motor torque sensitivity constant (lb ft/amp)
S=Scaling Factor To Convert SCOF (e.g. steel) To SCOF (e.g. TYVEK® brand material (dimensionless)

A measured reduction in motor current level is used as a trigger to initiate a belt cleaning cycle. When the motor current is reduced to a level equivalent to a SCOF of about 0.57, a signal is given to start the cleaning cycle.

FIG. 4 is a graph depicting the current versus time curve expected from the motor, during clockwise rotation (see FIG. 1) of the friction roller when in contact with the belt, during SCOF measurement. The maximum current value is shown as being equivalent to the maximum SCOF value of 0.65 at the threshold of slip between the roller and the conveyor belt surface.

The SCOF value of 0.65, is an actual (conservative) measured value for TYVEK® brand packaging material in contact with PVC belting material when the belts are new and uncontaminated. This same value can be reinstated after each cycle of the abrasive cleaning process.

By examining the motor current profile shown in FIG. 4, it is seen that the motor current will rise from a zero value at the instant the electrical clutch 16 is actuated to reverse the rotation of the friction roller. The current increases until the threshold of slip expected with the belt, is reached at a value equivalent to a SCOF value of approximately 0.65. Once slip is initiated, the current value will drop due to the fact that the DCOF is significantly lower than the SCOF with these materials. The constant current value shown in the drawing is used to measure the equivalent DCOF value, which in this case is approximately 0.030 less than the SCOF value.

FIG. 4 also shows examples of current values which identify a typical design range that can be used for TYVEK® and PVC belting material. This range is shown superimposed on the motor current curve, at a position lower than the maximum expected value. The top line of the range is identified as the upper design limit with a SCOF value of 0.65. The lower line of the range is identified as the lower design limit with a SCOF value of 0.55.

The cleaning cycle is initiated before the measured SCOF degrades to the lower limit of 0.55, (lowest quadrant of the design range) in order to assure that operation within the design range is preserved even during the cleaning cycle. A current value equivalent to a SCOF range between 0.55 and 0.57, is reasonable for initiating the cleaning cycle.

When measurement of the SCOF takes place during the belt cleaning cycle, a current value equivalent to a SCOF in the upper quadrant of the range is selected, in order to provide the maximum time between cleaning cycles. An SCOF value between 0.63 and 0.65 is reasonable, to stop the cleaning cycle.

The friction roller 1 is a key element in the measurement process. In this implementation the roller can be configured in the following ways:

(a) When the actual SCOF is to be measured, the surface of the roller will have an adhesively bonded layer of TYVEK® material on its periphery.
The measured value in this case will then be the actual SCOF of TYVEK® material and the conveyor belt, at the instant of slip.
This method would be of value primarily in the standalone SCOF measurement device, where the TYVEK® material would need periodic replacement due to contaminant transfer during slip.

(b) An alternate approach is used in the Conveyor Measurement And Cleaning System. In this case, a hardened stainless steel roller with a highly polished surface is used instead of the TYVEK® material. In this scheme, the steel roller resistance to slip when in contact with the PVC belting material is considerably greater than TYVEK® against PVC belting material. The motor current data using the steel roller data is then reduced by a scaling factor, to be representative of the conditions obtained with the use of the TYVEK® material. The scaling factor S is identified in the mathematical derivation for the SCOF presented above and also is shown in the system block diagram in FIG. 5.

The rationale for the use of this approach is that the hardened stainless steel roller is more reliable as a process control medium for long term service, and would not require periodic replacement, as the TYVEK® surface would.

The surface of the steel roller would also be very durable in this application. Also, the hard surface would not easily be coated by contaminants from the belt surface, as would be TYVEK® material, which is relatively soft. Contaminant materials transfer from the belt to the roller surface during the time of slip (relative motion). Using a stainless material would prevent rusting of the contact surface of the friction roller, which could affect friction measurement results. Also, under these test conditions, the steel roller in contact with a PVC belt under high normal force conditions, would be self cleaning.

Method of Applying the Required Normal Force

Several schemes are available for applying the normal force to the measurement roller:

The first method involves the use of a pivot arm and a weight. The value of the normal force would be calculated in advance and introduced in the process, as a constant. This method is relatively simple but is not as accurate as measuring the actual force, at the time of SCOF calculation.

The second method would use a strain gauge to measure the normal force in-process, and is a more accurate approach since it would eliminate the effect of any possible variations such as pivot friction or alignment, during operation. The strain gauge is shown in FIG. 1A, as item 37, and its location is directly below the yoke 14 of the friction measuring unit. The actuator drives the pivot arm directly in this case, without using a slotted connection. As the pivot arm 2 is raised to exert a force on the friction roller 1, the force compresses the strain gauge, before reacting on the friction roller. The input from the strain gauge is also shown in FIG. 5, in the NORMAL FORCE block.

The first method is shown in FIG. 1, and is explained in detail in the following description.

Friction roller 1 is mounted on a pivot arm 2, by low friction bearings 10 mounted in the yoke 14, which forms the end of the pivot arm on the friction roller end. The pivot arm is supported by a support bracket 4. The location of the pivot 8 on the arm is such that the distance between the pivot and the friction roller 1 and between the pivot and the weight 6 are equal. The functions of the pivot arm are described below:

(c) The equal distances of the pivot arm 2, convert the vertical (downwardly directed) gravity force of the weight 6, to an equal magnitude (upwardly directed) force at the centerline of the friction roller 1, in the position when the friction roller is brought into contact with the belt. The magnitude of the weight is selected on the basis of obtaining a "net" design value of normal force, after subtracting out the weight components of the motor 15, the clutch 16, friction roller 1, and other components.

Using a weight in the measurement process provides for the application of a defined and consistent normal force to the interface between the roller and the belt surface, and as such provides a necessary function in the process of measuring the SCOF.

(d) The second function of the pivot arm 2 is to provide an attachment for the drive pin 9, so that the linear actuator 3 can allow the pivot arm to rotate up when the actuator is de-energized.

The linear actuator 3 is electrically initiated, and provides the function of moving the pivot arm so that the friction roller is either in contact with the belt or is disconnected from contact with the belt.

The drive pin 9 is press fitted to the pivot arm in the position shown in FIG. 1. The drive pin projects from both sides of the pivot arm, to allow for a yoke 14 connection through the slot 7 in the linear actuator shaft 11.

The linear actuator is electrically powered. The lower portion of the actuator is mounted in support yoke 12, which allows the actuator to rotate slightly to adapt to pivot arm movement when the pivot arm is moved by the actuator. The linear actuator shaft 11, is slotted 7 at the coupling point with pin 9 in order to:

(e) Allow the weight 6 to move the pivot arm in the up direction. Electrical power is removed from the linear actuator to allow the weight to rotate the right side of the pivot arm in the down direction, so that the friction roller can contact the belt. Linear actuator 3 has an internal spring return means which pushes shaft 11 of the actuator upwardly to allow position "A" of arm 2 to be engaged (as shown) when linear actuator 3 is de-energized. Powering the linear actuator 3 downwardly to obtain position "B" of arm 2 also compresses the internal spring and therefore stores energy which is then released when the actuator is de-energized. This spring force then moves the shaft 11 upwardly to allow position "A" to take place. This type of linear actuator is known as a powered-in-one-direction and spring-return-in-the-opposite-direction device. The drive pin 9 is in the middle of the slot 7, when the friction roller is in contact with the belt. This feature permits the linear actuator to be completely free from applying any force to the friction roller during SCOF measurement, allowing only the weight 6 to apply the normal force. Also, the weight 6 is attached to pivot arm 2 by a self aligning hook 13, which provides for orienting the weight vertically, even though the pivot arm rotates. This feature assures that the force exerted by weight 6, is always vertical, and insures the consistency of the normal force value, being applied to the friction roller.

(f) When the friction roller is disconnected from contact with the belt at the end of the measurement cycle, the linear actuator is energized to pull the pivot arm to its lower position. In this mode, the top portion of the slot 7 is in contact with drive pin 9, to pull the pivot arm down. The linear actuator remains energized holding the pivot arm down under power, until the next measurement cycle is initiated.

Detailed Description of the Belt Cleaning Unit

For in-process cleaning, a dry brush roller must be used rather than any form of liquid cleaner. This is required because the belt surface cannot be wetted in any way since mail is being processed on the upper portion of the belt, and using liquid cleaners would lower the friction properties of the belt surface.

In order to effectively remove contaminants from the belt, a high relative velocity is required between the brush surface and the belt surface, to get scrubbing action. This is accomplished primarily by driving the brush in the opposite direction to the belt movement direction. The magnitude of the relative velocity is the sum of both the belt and brush peripheral velocities.

It may also be necessary to reverse direction of the brush roller periodically (cyclically), in order to dislodge firmly embedded particles attached to the belt surface. In this instance the forward velocity of the brush roller must exceed the belt velocity by at least 50% of the belt speed to be effective.

Description of the Belt Cleaning Problem

One specific problem that must be addressed in any automated system approach which uses SCOF data to actuate a belt cleaning unit, is to guarantee that the data which is obtained in one small area of the belt (as is the case with the measuring unit) is truly representative of the entire transporting surface area of the belt. The assumption made here is that the entire belt surface area is equally dirty as is the small area being measured. This problem is addressed by providing constant pressure along the full length of the brush roller, in order to assure that 100% coverage is obtained.

The following features are provided to create constant cleaning forces for the full width of the belt, during the cleaning process:

A means is provided to supply an easily variable, large force to the brush roller, which automatically compensates for inevitable brush wear. This feature provides a means to eliminate the constant manual readjustment of the brush contact with the belt, which would ordinarily be required.

A means is provided to supply a consistent force for the full length of the brush roller, which compensates for dimensional and parallelism variations between the plane of the belt and the plane of the brush roller. This problem must be addressed whether the system is automated or not. Essentially, the solution to this problem insures that measurement in one small area is in fact representative of the entire surface.

The belt cleaning unit is essentially composed of a motor driven brush roller 26 which is brought into contact with the belt, by using an air powered linear actuator (see FIGS. 1 and 3). Air pressure can easily bring a large and automatically variable force to bear across the entire belt width, which can be 20 inches wide in some applications. The brush roller is supported by two spherical bearings 34, mounted on the end of each brush support arm 19. The brush support arms pivot on fixed pivot pins 21 which are press fitted into the support frames 25.

The drive motor 27, is mounted on the base plate, and drives the brush roller through two synchronous timing belts. A pulley 28 mounted on the motor shaft drives the motor drive belt 29 which, in turn, drives the cluster pulley 30 which is also mounted on the drive side pivot pin 21. The cluster pulley has bearings which permit the pulleys to rotate in respect to the fixed pivot pin. The motor position allows for locating the relatively heavy motor in a stationary location, and provides only the relatively light brush roller and support arms to be pivoted by the air cylinders.

This arrangement provides the ability of running the motor to drive the brush roller, while simultaneously pivoting the rotating brush roller into contact with the moving belt, or to disengage the rotating brush roller. Belt 31 drives the brush rotation and also pivots about pin 21 when arm 19 is rotated alternately between positions "C" and "D".

The brush roller 26 is brought into contact with the belt by two air operated actuators 22, which drive the support arm through drive pins 20, and a sleeve bearing at each location. An electrically actuated three way valve is used to direct air pressure to the actuators, to either bring the brush roller into contact with the belt, or to disengage the brush roller.

The bristles in brush roller 26, are fastened to a relatively large diameter and thin walled steel tube (about 1.5 to 2.0 in.) which provides substantial rigidity to resist bending across the wide belt, when pressure is applied by the air cylinders. The brush support arms 19 motion is stopped only through contact with the conveyor belt, and remains in this position under constant pressure from the air cylinders. This is an important feature since it provides an automatic method for compensating for brush wear. As the brush wears, the actuator extends further to make brush contact with the belt. No manual adjustment is required to provide for brush wear compensation. This feature lends itself to fully automating the belt cleaning operation.

The purpose of supporting the brush roller with two spherical ball bearings (cartridge mounted, spherically aligned standard bearings can also be used), is to provide the capability of bringing the brush roller into full contact for the full width of the belt, under constant pressure, independent of any dimensional or parallelism variation of the brush or its mounting frame. This feature insures bringing constant brush pressure against the full width of the belt surface, and therefore assuring consistent, equal pressure cleaning across the full width of the belt.

This is a unique feature, which continuously provides for constant pressure on the full brush length, and also compensates for many variations that can take place throughout the life of the unit, such as non uniform brush wear, possible variations in setup of components, and belt thickness variations which can occur during manufacture of the belt splice point. This feature further provides for the full automation of the conveyor belt cleaning function.

Basically, the independently actuated support arms will operate separately to make contact with the belt surface, so that parallelism variations in the support surface relative to the line of contact of the brush, will not affect achieving full contact of the brush with the belt. This is made possible by the spherical bearings 34 which provide for the somewhat limited independent actuation of the support arms, when contact with the belt is made. If a non parallel condition exists, the axis of the brush roller will assume a slightly non perpendicular position with respect to the direction of belt motion, by providing for one arm to move higher than the other. The slight non perpendicular position of the brush relative to the direction of belt motion will have no negative effect on cleaning the belt. This ability is limited to the degree of self alignment available in the bearings.

Removal of Debris Resulting from the Cleaning Process

The abrasive belt cleaning process will produce particles of paper and belt dust which must be removed, to prevent polluting the air, and possibly affecting machinery operation adversely. This is done by using a vacuum removal system, which is continuously operating when the brush is in contact with the belt during the cleaning cycle. A shroud 38 envelops the cleaning brush, providing for a vacuum pump 36 to create a low pressure which will pull the removed particles through a tube 35 into a filter unit, for removal during down time maintenance periods.

Figure 7:
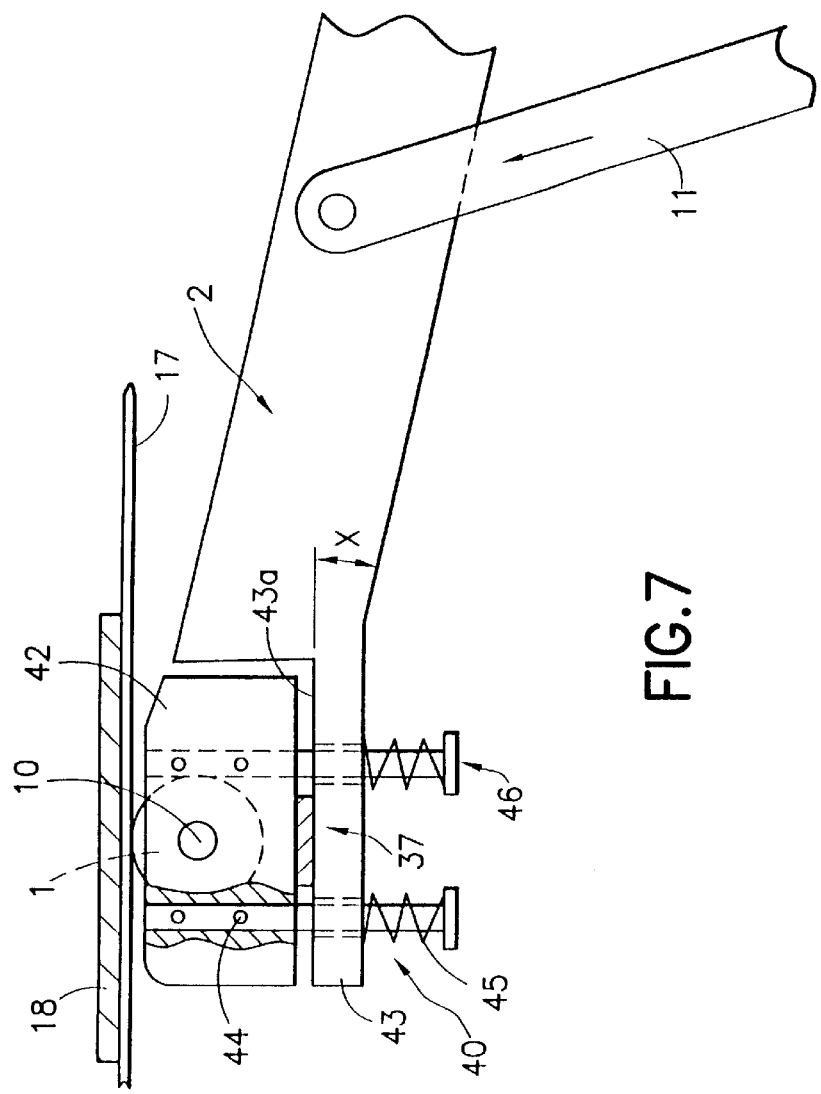
FIG. 7 is a detail side elevation view of the embodiment illustrated in FIG. 6.
Figure 6:
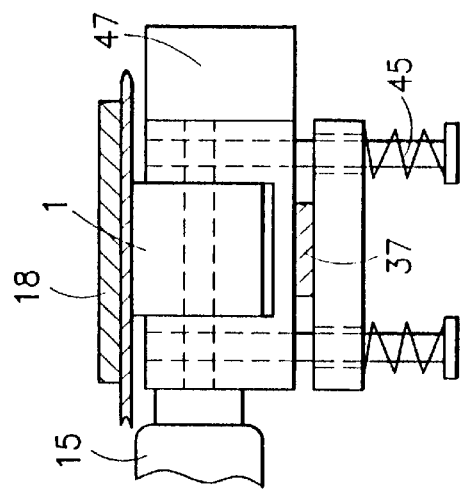
FIG. 6 is a detail end elevation view of another embodiment of the invention.

Turn now to FIGS. 6 and 7 for the description of another embodiment of the invention which utilizes a load cell 37 in order to obtain an accurate measurement of the SCOF. The load cell mounting is defined in detail since the mounting is very important relative to obtaining the desired result of accurately measuring the normal force. Accurate measurement of normal force is the key to obtaining accurate results for the Static Coefficient Of friction (SCOF). Load cells are commercially available devices, which are commonly used as transducers in weighing scales, where the force is applied in compression. Load cells are typically composed of a metal frame which has a strain gauge attached to the frame. The frame can be loaded in compression, and is designed in such a way that the strain gauge will be stressed in tension when the frame is stressed in compression. Load cells are available with measurement accuracy of approximately 0.1% of the force being measured. FIGS. 6 and 7 illustrate two views of a mounting that would satisfy the requirements of the invention.

The load cell mounting surface must be parallel to the plane of the belt 17 being measured in order to eliminate the need to calculate component forces in the normal force determination. This feature is obtained by machining a support surface 43*a* on an extremity 43 of the pivot arm 2 at an angle X with respect to the arm such that the surface is now parallel with the plane of the belt being measured, as shown in FIG. 6. Therefore, the reaction force between the roller 1 and the belt 17 is perpendicular to the load cell 37, as required to obtain an accurate normal force measurement.

In order to measure the normal force accurately, all forces bearing on the load cell 37, or on a yoke block assembly 40 rotatably mounting the roller 1 other than the normal force, must either be eliminated or their value determined and subtracted from the total force being measured. The following discussion identifies these "extraneous" forces which must be determined in order to obtain a value of just the normal force.

The extraneous forces which would need to be addressed are: the weight force of all of the components beating down on the load cell, friction forces which would result if the weight force is not balanced, and spring forces which will be necessary to stabilize the mounting of the yoke block assembly 40 in its new mounting configuration. The stabilization method provides necessary rigidity during operation, while at the same time provides an accurate measure of the holding force provided.

To this end, the roller 1 is preferably slidably mounted in order to provide for the capability of vertical movement of the yoke assembly when transferring the reaction force to the load cell. This arrangement also provides the ability to accurately determine the magnitude of all weight and spring forces, which must be subtracted from the total force being measured in order to obtain the normal force. The magnitude of the weight and spring forces will be determined after device assembly is completed and before contact of the roller 1 is made with the belt 17, by merely recording the total value in the reading of the load cell (with electrical power turned "on"), and prior to application of the device actuation force via the air cylinders. This value is then subtracted (in the computer) from the total recorded force obtained from the load cell during operation, to yield the required normal force. It is noteworthy that the amount of vertical movement of the yoke block assembly 40 during contact with the belt 17 (during use) is insignificant and therefore the initial preload force of the springs remains essentially the same during operation of the device.)

The yoke block assembly 40 really comprises the roller 1, a yoke block 42, the motor 15, and all the associated drive components. This arrangement is supported by four dowels 44, which are pinned to the yoke block 42 but are slidably mounted on an extremity 43 of the pivot arm 2 as shown in FIG. 7. The slidable mounting on the extremity 43 of pivot arm 2 utilizes low friction bearings to further reduce any minor frictional forces which could additionally cause errors in determining the normal force.

Since the motor 15 and other components are cantilevered relative to the slidable dowels 44, this arrangement would apply an eccentric load on the roller assembly. In order to prevent this eccentric load from creating unwanted friction forces at the position of the dowels during operation, the yoke block assembly 40 must then be balanced with a counterweight 47 (FIG. 6) on the opposite side of the yoke. The counterweight 47 serves to shift the center of gravity so that it resides in the center of the roller, or directly over the load cell 40. This would remove any moment or eccentric load about the roller due to the cantilevered motor 15 and, therefore, eliminates any moment related friction forces brought to bear against the dowels during operation. There is no significant eccentric load in the transverse direction, since the yoke block 42 can easily be designed to obtain a balanced condition in this direction.

In order to obtain a stable mounting for the motor 15 and the yoke block assembly 40, a compression spring 45 is provided, encircling each dowel 44. The four springs are preloaded on assembly in order to provide a resilient stabilizing force for the motor and roller assembly. A shoulder 46 on each dowel 44 permits the compression force of the springs 45 to react on the lower portion of arm 2 and to pull the yoke block assembly 40 against the load cell. With this arrangement, the springs are preloaded to a value which obtains the desired yoke assembly stability and the total spring preload, and weight, force is subtracted from the total measured force.

This subtraction is intended to take place in a "force subtracter" unit shown in the block diagram of FIG. 5 beneath the load cell 37. The function of the subtract unit is to accept the total force as measured by the load cell and to subtract the value of the preload force in the four springs as well as the total weight of the yoke block assembly 40, which was determined before the unit was assembled. The subtracter solves the equation $N=F_t-(F_s+F_w)$ where $F_t$ is the total force, $F_s$ is the spring preload force, and $F_w$ is the weight force of all of the components bearing on the load cell (which includes primarily the roller and support. The output of the subtracter is then equal to the required normal force and is then used in the calculator to determine the SCOF. The output of the subtracter is now identical to the force being applied to the belt 17 by the roller 1. The forces applied to the load cell during operation are $F_t=F_1-(F_s+F_w)$ where $F_t$ is the total force measured by the load cell, where $F_s$ is the total spring preload force, $F_w$ is the total weight force of the yoke block assembly 40, $F_1$ is the perpendicular component of the force applied by the cylinder and N is the output force recorded by the subtracter.

As applicants proceeded to define the invention, they recognized that the load cell component 37 utilizing a strain gauge must be described accurately, in order to define how it will be configured to measure the total force on the roller 1, a force which will be transmitted in compression. Normally, a strain gauge is used to measure applied forces when the load is transmitted to the gauge in tension. However, strain gauge devices are commercially available which can be used in compression applications. These devices are generally referred to as load cells, and are frequently used for weight measurement in electronic scales. In effect, the load cell converts a compressive load to a tensile load (required by the load cell), generally using some form of mechanical beam mounting arrangement. Load cells used in scales are extremely accurate since they are calibrated to measure to an accuracy of at least 0.1% of the applied load. This is well within the accuracy required for purposes of the present invention.

While preferred embodiments of the invention have been disclosed in detail, it should be understood by those skilled in the art that various other modifications may be made to the illustrated embodiments without departing from the scope of the invention as described in the specification and defined in the appended claims.

What is claimed is:

1. In combination with an operating conveyor belt including a conveyor surface moving in an advancing direction and having a static coefficient of friction (SCOF) of a magnitude within a range capable of measurement, apparatus for measuring the magnitude of the SCOF of the surface thereof comprising:

a friction roller rotatable about a friction roller axis perpendicular to the direction of movement of the conveyor belt;

friction roller actuator means for moving said friction roller between a retracted position disengaged from the conveyor belt and an engaged position rotatably engaged with the conveyor belt;

a friction roller drive motor means drawing electrical current from an EMF source selectively operable, in one instance, for permitting free wheeling rotation of said friction roller when rotatably engaged with the conveyor belt and, in another instance, for rotating said friction roller about the friction roller axis in a direction opposite the advancing direction of movement of the conveyor belt;

sensing means for continuously sensing the magnitude of the current drawn by the friction roller drive motor and relating that as an output; and computer means responsive to the output of said sensing means when the magnitude of the current reaches a maximum value for calculating the SCOF of the surface of the conveyor belt, the SCOF being a function of the magnitude of the maximum value of the current drawn by the friction roller drive motor.

2. Apparatus as set forth in claim 1 wherein said friction roller actuator means includes:

a base member including an upstanding support bracket;

a pivot arm extending between first and second ends and pivotally mounted to an upper end of said support bracket intermediate said first and second ends;

yoke means at said first end for rotatably supporting said friction roller; and weight means at said second end for biasing said friction roller into engagement with the conveyor belt while imparting a defined and consistent normal force.

3. Apparatus as set forth in claim 2 wherein said friction roller actuator means includes an elongated actuator and an actuator rod operated thereby, said actuator being pivotally mounted at one end on said base member and slidably connected at the opposite end with said pivot arm intermediate said first end and said upper end of said support bracket for normally holding said friction roller out of engagement with the conveyor surface and operable for releasing said friction roller for movement into engagement with the conveyor surface, being biased by said weight means.

4. Apparatus as set forth in claim 2 wherein said weight means includes:
   a weight member; and
   a self-aligning hook suspending said weight member such that the force imparted by said weight member is always vertical.

5. Apparatus as set forth in claim 2 wherein said friction roller drive motor means includes:
   a friction roller drive motor; and
   clutch means movable between a first position whereat said friction roller drive motor is disengaged from said friction roller and a second position whereat said friction roller drive motor is engaged with said friction roller.

6. Apparatus as set forth in claim 5 including:
   a tachometer for sensing rotational speed of said friction roller and generating an output signal proportional thereto;
   said friction roller drive motor being responsive to the output signal of a predetermined magnitude from said tachometer for moving said clutch means from the first position to the second position.

7. Apparatus as set forth in claim 5 including:
   a timer generating an output signal proportional to time;
   said friction roller drive motor being responsive to the output signal of said timer after a predetermined time interval for moving said clutch means from the first position to the second position.

8. Apparatus as set forth in claim 2 wherein said friction roller actuator means includes an elongated actuator and an actuator rod operated thereby, said actuator being pivotally mounted at one end on said base member and said actuator rod being pivotally connected with said pivot arm intermediate said first end and said upper end of said support bracket for normally holding said friction roller out of engagement with the conveyor surface and operable for releasing said friction roller for movement under the bias of said weight means into engagement with the conveyor surface; and including:
   load cell means intermediate said pivot arm and said friction roller for sensing the force imparted by said friction roller against the conveyor belt and operable to generate a force signal proportional thereto, said computer means being responsive to the force signal for calculating the SCOF of the surface of the conveyor belt, the SCOF also being a function of the force imparted by said friction roller against the conveyor belt.

9. Apparatus as set forth in claim 1 for measuring the static coefficient of friction (SCOF) of the surface of an operating conveyor belt, then for cleaning the conveyor belt comprising:
   a brush roller rotatable about a roller axis perpendicular to the advancing direction of movement of the conveyor belt for cleaning the surface of the conveyor belt;
   brush roller actuator means for moving said brush roller between a retracted position disengaged from the conveyor belt and an engaged position rotatably engaged with the conveyor belt; and
   a brush roller drive motor means for rotating said brush roller about the brush roller axis when said brush roller is engaged with the conveyor belt.

10. Apparatus as set forth in claim 9 wherein said brush roller actuating means is responsive to said computer means for moving said brush roller to the engaged position when the SCOF has a value within the range of about 0.55 and about 0.57; and
    wherein said brush roller actuating means is responsive to said computer means for moving said brush roller away from the engaged position when the SCOF is within the range of about 0.63 and about 0.65.

11. Apparatus as set forth in claim 9 including:
    a pair of laterally spaced upstanding support brackets on said base member;
    a brush roller pivot arm extending between first and second ends and pivotally mounted to an upper end of each of said support brackets at said first end:
    said brush roller extending between opposed ends, said opposed ends being rotatably supported on said second ends of said brush roller pivot arms; and
    wherein said brush roller actuator means is elongated and is pivotally mounted with said brush roller pivot arm intermediate said first and second ends for normally holding said brush roller out of engagement with the conveyor surface and operable in response to said computer means for moving said brush roller into engagement with the conveyor surface.

12. Apparatus as set forth in claim 9 including:
    spherical ball bearings rotatably supporting said opposed ends of said brush roller on said second ends of said brush roller pivot arms.

13. Apparatus as set forth in claim 9 including:
    vacuum means adjacent said conveyor belt and said brush roller continuously operating when said brush roller is in engagement with said conveyor belt for removing particulate material resulting from the surface cleaning operation.

14. Apparatus as set forth in claim 13 wherein said vacuum means includes:
    a shroud enveloping said brush roller;
    a vacuum pump for creating a low pressure within said shroud to draw the particulate matter away from the surface of the conveyor and said brush roller; and
    a tube connecting said vacuum pump to said shroud.

15. Apparatus as set forth in claim 1 for measuring the static coefficient of friction (SCOF) of the surface of an operating conveyor belt, then for cleaning the surface of an operating conveyor belt comprising:
    a brush roller rotatable about a roller axis perpendicular to the direction of movement of the conveyor belt for cleaning the surface of the conveyor belt;
    brush roller actuator means for moving said brush roller between a retracted position disengaged from the conveyor belt and an engaged position rotatably engaged with the conveyor belt; and
    a brush roller drive motor means for rotating said brush roller about the brush roller axis when said brush roller is engaged with the conveyor belt.

16. Apparatus as set forth in claim 15 wherein said brush roller actuating means is responsive to said computer means for moving said brush roller to the engaged position and for moving said brush roller away from the engaged position.

17. Apparatus as set forth in claim 15 including:
a pair of laterally spaced upstanding support brackets on said base member;
a brush roller pivot arm extending between first and second ends and pivotally mounted to an upper end of each of said support brackets at said first end;
said brush roller extending between opposed ends, said opposed ends being rotatably supported on said second ends of said brush roller pivot arms; and
wherein said brush roller actuator means is elongated and is pivotally mounted at the opposite end with said brush roller pivot arm intermediate said first and second ends for normally holding said brush roller out of engagement with the conveyor surface and operable in response to said computer means for moving said brush roller into engagement with the conveyor surface.

18. Apparatus as set forth in claim 15 including:
spherical ball bearings rotatably supporting said opposed ends of said brush roller on said second ends of said brush roller pivot arms.

19. Apparatus as set forth in claim 15 including:
vacuum means adjacent said conveyor belt and said brush roller continuously operating when said brush roller is in engagement with said conveyor belt for removing particulate material resulting from the surface cleaning operation.

20. Apparatus as set forth in claim 19 wherein said vacuum means includes:
a shroud enveloping said brush roller;
a vacuum pump for creating a low pressure within said shroud to draw the particulate matter away from the surface of the conveyor and said brush roller; and
a tube connecting said vacuum pump to said shroud.

21. Apparatus for cleaning the surface of an operating conveyor belt including a conveyor surface moving in an advancing direction and having a static coefficient of friction (SCOF) of a magnitude within a range capable of measurement comprising:
a friction roller rotatable about a friction roller axis perpendicular to the advancing direction of movement of the conveyor belt rotatably engaged with the surface of the conveyor belt;
a friction roller drive motor capable of drawing electrical current up to a maximum current for rotating said friction roller about the friction roller axis in a rotating direction opposite the advancing direction of movement of the conveyor belt;
sensing means for continuously sensing the magnitude of the current drawn by the friction roller drive motor and relating that magnitude as an output; and
computer means responsive to the output of said sensing means when the output of said sensing means reaches a maximum value for calculating the static coefficient of friction (SCOF) of the surface of the conveyor belt, the SCOF being a function of the maximum current drawn by the friction roller drive motor;
a brush roller rotatable about a roller axis perpendicular to the direction of movement of the conveyor belt for cleaning the surface of the conveyor belt;
brush roller actuator means for moving said brush roller between a retracted position disengaged from the conveyor belt and an engaged position rotatably engaged with the conveyor belt; and
a brush roller drive motor means for rotating said brush roller about the brush roller axis when said brush roller is engaged with the conveyor belt.

22. Apparatus as set forth in claim 21 wherein said brush roller actuating means is responsive to said computer means for moving said brush roller to the engaged position when the SCOF has a value within the range of about 0.55 and about 0.57; and
wherein said brush roller actuating means is responsive to said computer means for moving said brush roller away from the engaged position when the SCOF is within the range of about 0.63 and about 0.65.

23. Apparatus as set forth in claim 21 including:
a base member;
a pair of laterally spaced upstanding support brackets on said base member;
a brush roller pivot arm extending between first and second ends and pivotally mounted to an upper end of each of said support brackets at said first end;
said brush roller extending between opposed ends, said opposed ends being rotatably supported on said second ends of said brush roller pivot arms; and
wherein said actuator means is elongated and is pivotally mounted at the opposite end with said brush roller pivot arm intermediate said first and second ends for normally holding said brush roller out of engagement with the conveyor surface and operable in response to said computer means for moving said brush roller into engagement with the conveyor surface.

24. Apparatus as set forth in claim 23 including:
spherical ball bearings rotatably supporting said opposed ends of said brush roller on said second ends of said brush roller pivot arms.

25. Apparatus as set forth in claim 21 including:
vacuum means adjacent said conveyor belt and said brush roller continuously operating when said brush roller is in engagement with said conveyor belt for removing particulate material resulting from the surface cleaning operation.

26. Apparatus as set forth in claim 25 wherein said vacuum means includes:
a shroud enveloping said brush roller;
a vacuum pump for creating a low pressure within said shroud to draw the particulate matter away from the surface of the conveyor and said brush roller; and
a tube connecting said vacuum pump to said shroud.

27. A system for selectively cleaning the surface of a conveyor belt including a conveyor surface moving in an advancing direction and having a static coefficient of friction (SCOF) of a magnitude within a range capable of measurement comprising:
friction measuring means for measuring the magnitude of the coefficient of friction of the surface of the conveyor belt and operable to generate a signal when the coefficient of friction as measured reaches a predetermined magnitude; and
conveyor belt cleaning means movable between a disengaged position distant from the conveyor belt and an engaged position in engagement with the surface of the conveyor belt, said belt cleaning means being responsive to the signal from said friction measuring means for moving from the disengaged position to the engaged position.

28. A system as set forth in claim 27 wherein said friction measuring means includes:
a friction roller rotatable about a friction roller axis perpendicular to the advancing direction of movement of the conveyor belt;

friction roller actuator means for moving said friction roller between a retracted position disengaged from the conveyor belt and an engaged position rotatably engaged with the conveyor belt;

a friction roller drive motor capable of drawing electrical current up to a maximum current selectively operable, in one instance, for permitting free wheeling rotation of said friction roller when rotatably engaged with the conveyor belt and, in another instance, for rotating said friction roller about the friction roller axis in a direction opposite the direction of movement of the conveyor belt;

sensing means for continuously sensing the current drawn by the friction roller drive motor and relating that as an output; and computer means responsive to the output of said sensing means when the output of said sensing means reaches a maximum value for calculating the SCOF of the surface of the conveyor belt, the SCOF being a function of the maximum current drawn by the friction roller drive motor.

29. A system as set forth in claim 27 wherein said friction roller actuator means includes:

a base member including an upstanding support bracket;

a pivot arm extending between first and second ends and pivotally mounted to an upper end of said support bracket intermediate said first and second ends;

yoke means at said first end for rotatably supporting said friction roller; and weight means at said second end for biasing said friction roller into engagement with the conveyor belt while imparting a defined and consistent normal force.

* * * * *